United States Patent
Anwar et al.

[11] Patent Number: 5,830,194
[45] Date of Patent: Nov. 3, 1998

[54] POWER SYRINGE

[75] Inventors: Azam Anwar, 4331 Arcady, Dallas, Tex. 75205; Christopher M. Boykin, Henderson, Tex.

[73] Assignee: Azam Anwar, Dallas, Tex.

[21] Appl. No.: 717,110

[22] Filed: Sep. 20, 1996

[51] Int. Cl.$^6$ ................................................ A61M 5/315
[52] U.S. Cl. ............................................ 604/223; 604/233
[58] Field of Search .................................. 604/181, 183, 604/184, 185, 187, 188, 223, 224, 233, 234, 235

[56] References Cited

U.S. PATENT DOCUMENTS

| | | | |
|---|---|---|---|
| 530,187 | 12/1894 | Laskey | 604/223 |
| 900,565 | 10/1908 | Mayers et al. . | |
| 2,773,500 | 12/1956 | Young . | |
| 4,014,331 | 3/1977 | Head | 604/223 X |
| 4,090,639 | 5/1978 | Campbell et al. | 604/223 X |
| 4,737,151 | 4/1988 | Clement . | |
| 4,854,324 | 8/1989 | Hirschmann et al. . | |
| 5,135,507 | 8/1992 | Haber et al. . | |
| 5,228,883 | 7/1993 | Blakely et al. . | |
| 5,288,285 | 2/1994 | Carter | 604/187 X |
| 5,336,201 | 8/1994 | von der Decan | 604/223 |
| 5,350,365 | 9/1994 | De Godoy Moveira | 604/187 |
| 5,368,578 | 11/1994 | Covington et al. | 604/187 X |
| 5,507,730 | 4/1996 | Haber et al. . | |
| 5,591,135 | 1/1997 | Sullivan . | |

*Primary Examiner*—Danton D. DeMille
*Attorney, Agent, or Firm*—Tobor & Goldstein, L.L.P.

[57] ABSTRACT

A power syringe (10) for use in medical procedures, such as angiography, delivers air or fluid, such as contrast medium, to a patient at operator controlled rates and pressures. In one embodiment, mechanical advantage is created by first and second arms (22, 26) which are interconnected with each other, the base, and the plunger (20). The proximal end of the syringe contains a track (44) that the plunger follows in normal fashion in and out of the reservoir. The track is bevelled from proximal to distal end to create a path with variable resistance. A mechanical stop (42) is at the proximal end of the track to control the length of travel of plunger and secondary mechanical arm. Markings (18) on reservoir (12) indicate the volume of fluid or air in the reservoir. Mechanical arm length, tracking length, and distance to plunger stop will vary with size of syringe to generate appropriate flow and power.

10 Claims, 3 Drawing Sheets

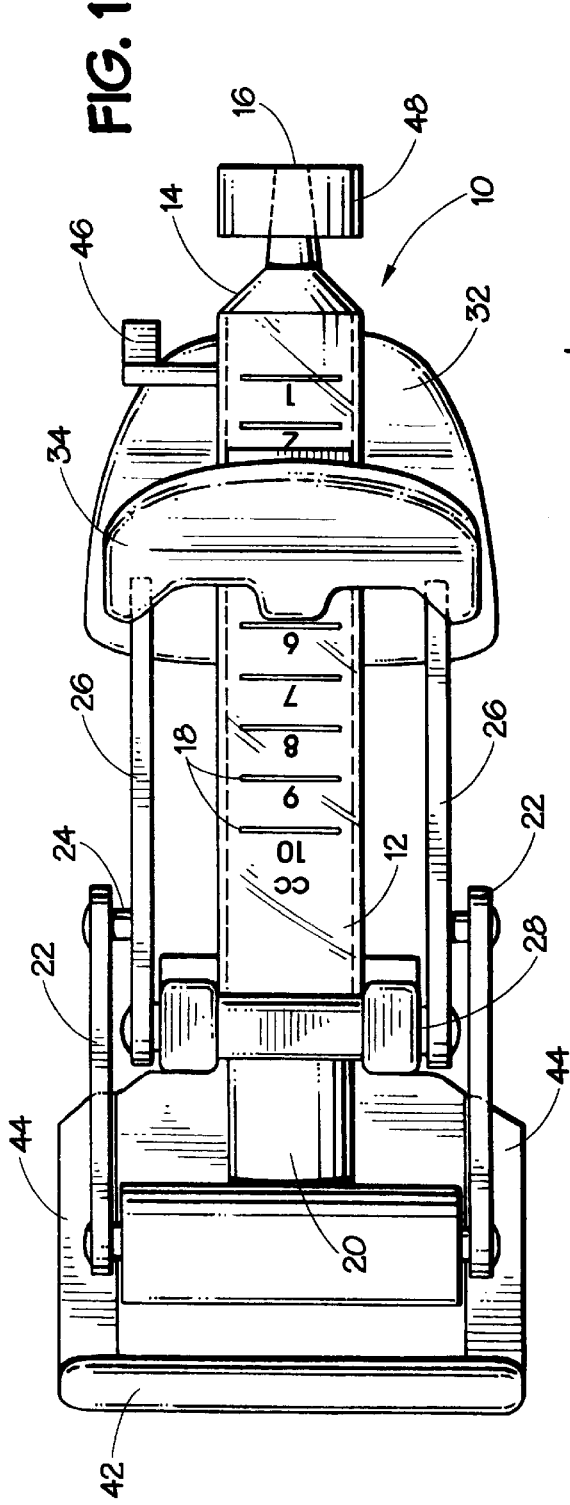
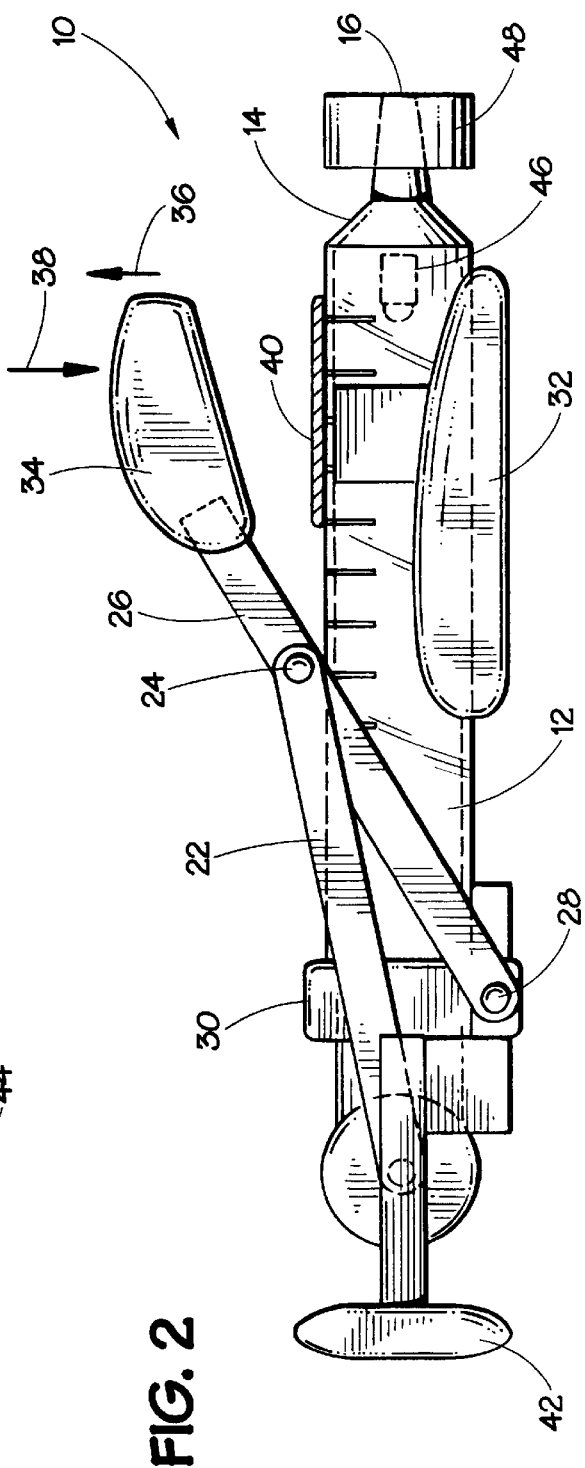

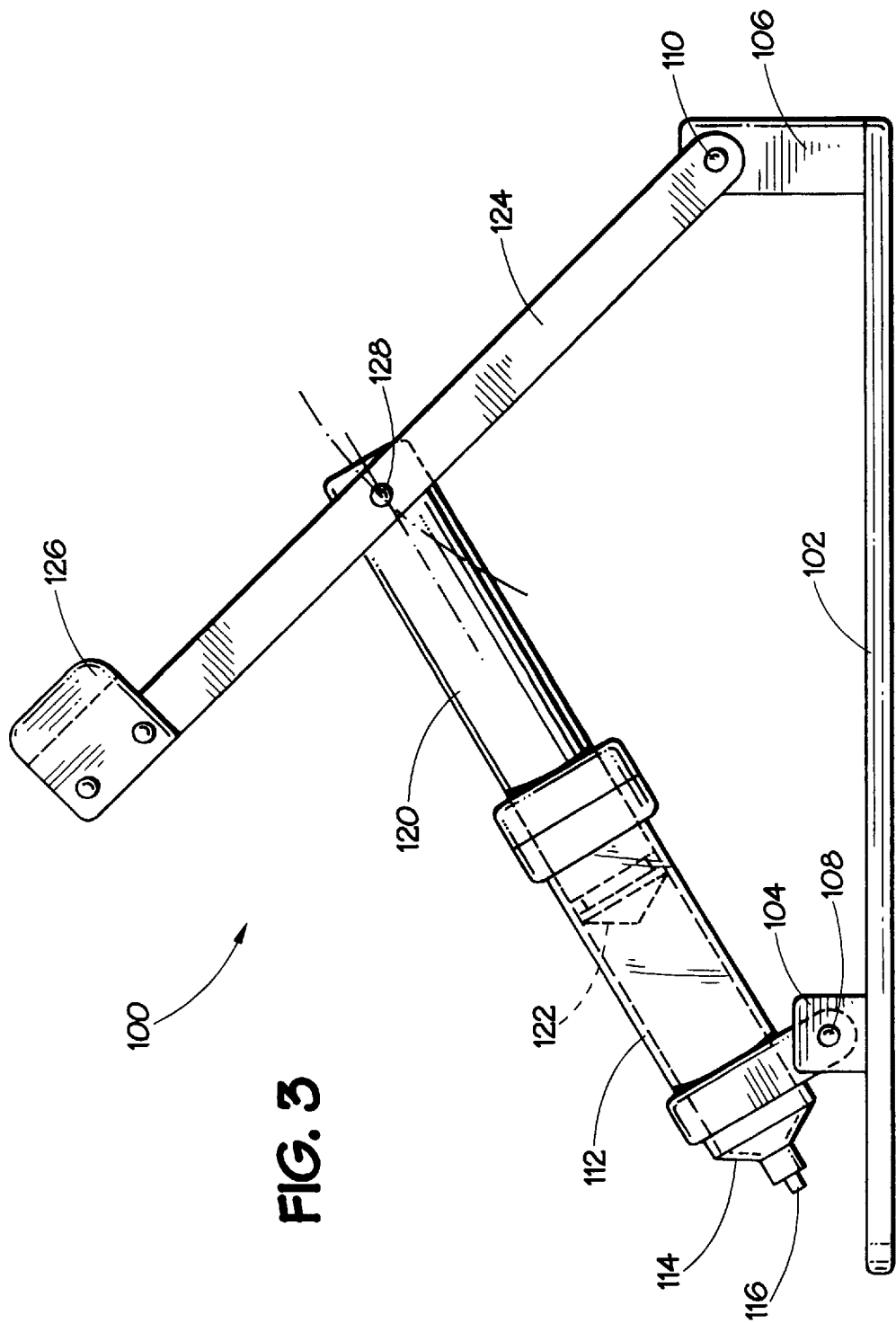

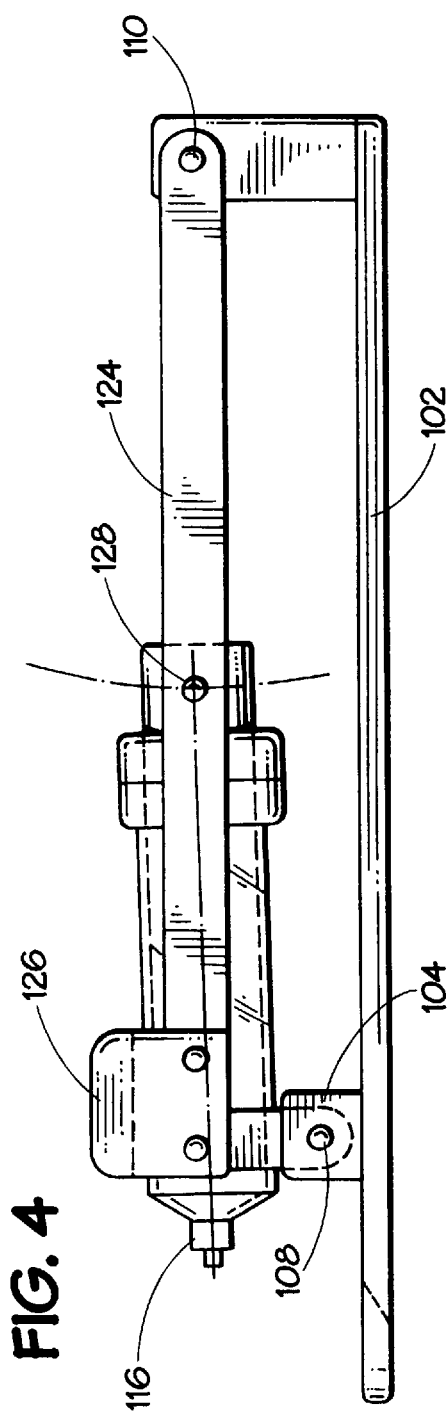
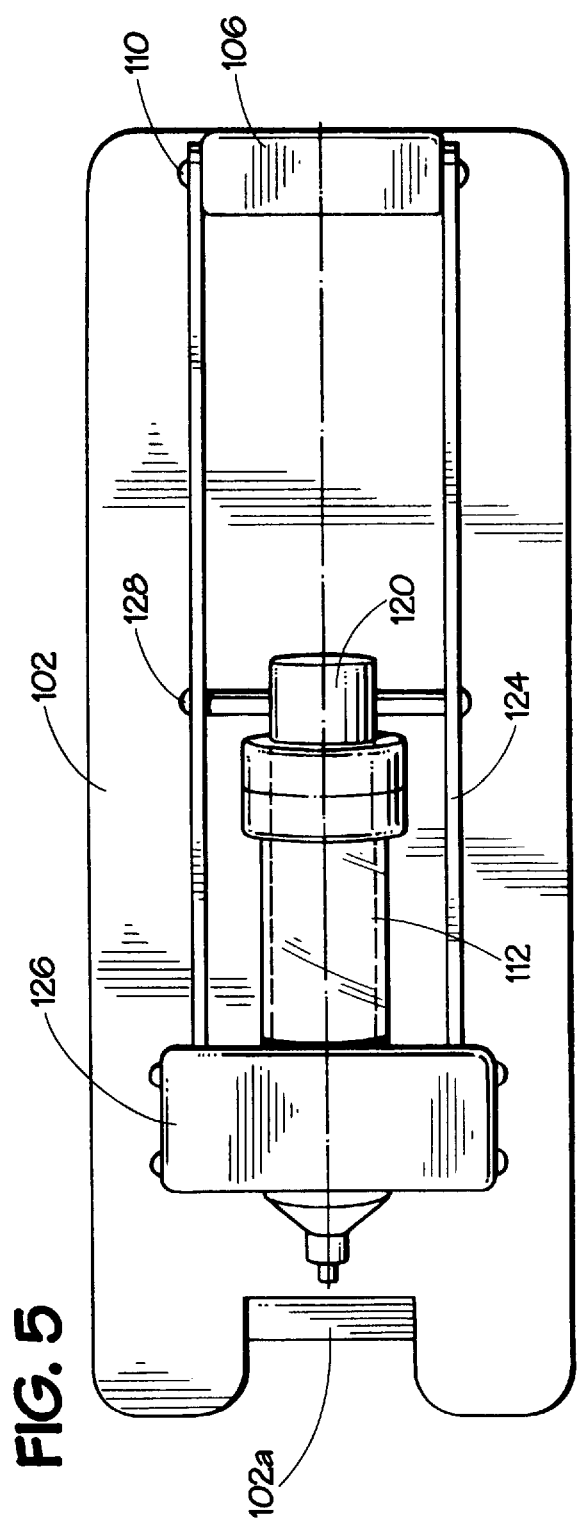

POWER SYRINGE

TECHNICAL FIELD OF THE INVENTION

The power syringe is used to inject a fluid or air into a patient. The power syringe provides significant mechanical advantage to the user, allowing a greater pressure stroke than achievable with a standard syringe.

BACKGROUND OF THE INVENTION

The invention pertains to a device for injecting into a patient a fluid, such as contrast medium, or air at a mechanically controlled rate and pressure during diagnostic or therapeutic procedures, such as angiography or other interventional procedures. Coronary angiography, for example, can be performed using either a manual syringe or driven by a power injector. Physicians can manually deliver contrast medium into small vessels using small syringes. However, angiography of large vessels and vascular chambers (left atrium, left ventricle, aorta, cerebral vessels, renal arteries, upper extremity vessels, vena cavae, lower extremity vessels, right atrium, right ventricle, and pulmonary arteries) requires more physical power than an operator can reasonably and accurately supply to prior art syringes. In these cases, a motorized mechanically powered angiographic injector system is typically used to inject the contrast medium.

It is very important that the proper amount of contrast medium, as well as the pressure and rate at which it is delivered, be controlled for safe and desirable results to both the operator and especially the patient. The prior art is exemplified in U.S. Pat. No. 4,854,324 to Hirschman et al. which discloses a large, cumbersome motor driven device. A technician has to position this large system close to the patient and clear air from the system, along with any particulate material. The physician instructs the technician with specific injection parameters. The parameters are then entered into the controls of the device and the device is activated. Once activated there is no way to stop the injection and the physician is not in control of the process. Also, the sudden force of injection can cause the catheter to become displaced or cause cardiac arrhythmia or injury to the vascular cavity. The system is cumbersome to load and unload with contrast medium and requires the use of an excess volume of contrast medium. Consequently there is consistent waste of expensive contrast material.

A need exists for a manually-controlled power syringe that incorporates mechanical advantage into the plunger. Such a power syringe should allow for easy monitoring of air or fluid flow. Likewise, the power syringe should provide the user with control to immediately stop the flow or to reinitiate the flow. Most importantly, the power syringe should be small and designed such that an unassisted user can operate the device without the help of others.

SUMMARY OF THE INVENTION

The present invention relates to an improved and manually operated power syringe that addresses the deficiencies in the prior art. In one embodiment, the power syringe has a cylindrical reservoir for receiving fluid such as contrast medium. A plunger is captured within the reservoir and is translatable therein. The plunger is attached to a first arm. The first arm is in turn attached to a central portion of a second arm. The second arm is pivotally attached to the base of the power syringe. Thus, when the other end of the second arm is pressed down, it results in the movement of the plunger forward in the syringe, injecting the fluid or air. The mechanical arms amplify the user's downward force on the second arm, thereby creating greater injection pressure.

The power syringe also features mechanical stops to limit the downward motion of the second arm, as well as the rearward motion of the plunger. A side port is used to allow any unwanted air captured within the reservoir to be expelled prior to injection of fluid into the patient. A series of volume indicators are also marked onto the cylindrical reservoir to allow the user to monitor the volume of fluid or air being injected.

In a second embodiment, the syringe is pivotally mounted on a base. A plunger is slidably captured within the syringe. A lever arm is pivotally attached to the other end of the base. The plunger is also attached to a central portion of the lever arm. Thus, when the lever arm is raised, the plunger is pulled back through the syringe, allowing it to fill. The syringe pivots in response to the movement of the lever. To inject the fluid in the syringe, the lever is pressed down. The lever arm amplifies the user's downward force on the plunger, thereby creating greater injection pressure.

BRIEF DESCRIPTION OF THE DRAWINGS

For a more complete understanding of the present invention, and for further details and advantages thereof, reference is now made to the following Detailed Description taken in conjunction with the accompanying drawings, in which:

FIG. 1 illustrates a top view of a power syringe embodying the present invention;

FIG. 2 illustrates a side view of the power syringe in FIG. 1; and

FIGS. 3, 4 and 5 illustrate an alternative embodiment of the invention.

DETAILED DESCRIPTION OF THE DRAWINGS

A power syringe 10 embodying the present invention is illustrated in FIGS. 1 and 2. The syringe 10 has a main reservoir 12 for receiving fluid. The reservoir 12 is generally a cylindrical tube which can have a luer distal end 14 encompassed by a stationary threaded connector 48. An opening 16 is present in the distal end 14. The reservoir 12 can be made out of a clear or partially transparent material so that the fluid contained therein is visible. Also, a series of markings 18 can be placed on the outer surface of the tube to indicate the volume of fluid or air contained within the reservoir.

A plunger 20 or piston is slidably captured within the reservoir. The plunger must be sized to prevent leakage despite the higher pressures generated by the power syringe. The plunger is pivotally attached to a first arm 22. The first arm is attached to a central portion 24 of a second arm 26. The second arm is pivotally attached to a first end 28 to first base 30. The first base 30 is rigidly attached to the reservoir near its proximal end. A second base 32 can be rigidly attached to the reservoir near its distal end. A palm pad 34 is located on the distal end of the second arm 26. The pad can be ergonomically designed to fit the palm or fingers of the user. The first base supports the syringe and provide stability as the syringe is loaded or unloaded. The base is wider than the syringe to decrease the torque effect that the syringe might experience during usage. The base can be made of the same plastic as the syringe, but contains a slightly abrasive surface to create more coefficient of friction between the syringe and the surface it is placed upon. The base also can contain finger indentations to allow for more control by the operator during usage.

In use, the opening 16 can be coupled to a supply of fluid (not shown). The pad 34 can be lifted, as indicated by arrow 36. Lifting of the pad forces the plunger away from the opening, thereby filling the reservoir. A side port 46 allows for de-airing during the loading and unloading of the reservoir to remove air during procedures requiring injection of fluid. As fluid, such as contrast medium, is brought into the reservoir and connecting tubing, the fluid is then pushed forward with the port 46 in an open position and air is dispelled without wasting fluid. The reservoir is now loaded and ready for the procedure. The fluid can then be injected into the patient by pressing down on the pad 34 as indicated by arrow 38. The travel of the pad is limited by a mechanical stop 40. The mechanical stop 40 can be placed at the downstroke of the palm pad and lever to match the position where the plunger bottoms out with the distal end of the inside of the reservoir. This prevents undue additional stress applied to the arm system during a procedure, and makes it easier for the user to feel when the reservoir is completely empty. Likewise, a plunger stop 42 can be provided to limit the rearward travel of the plunger 20. The plunger's linear travel can be maintained by a plunger track 44. The plunger track 44 can be bevelled and angled along the inside of the track to create a variable resistance path the plunger will follow. This is the method to eliminate the possibility of extreme pressures being developed during this manual procedure. The plunger track also gives the operator better control during the procedure to help with safety and comfort of the patient during the procedure. Since the operator will be able to control the flow, the fluid can be administered or stopped at any time during the procedure. The pressure, speed, and flow can also be varied at any time as deemed necessary for the success of the procedure.

The use of the first and second arms 22, 26 provides a significant mechanical advantage to the user. The length and connection of the armature assembly can, of course, be varied to alter the amount of mechanical advantage provided to the user. Generally, the effort of the user will be magnified according to the ratio of the downward travel of the pad 34 to the forward travel of the plunger.

An alternate power syringe 100 is illustrated in FIGS. 3, 4 and 5. The power syringe 100 has a reservoir 112 with a plunger 120 slidably mounted therein, and a base 102. The base 102 has first flange 104 and a second flange 106. The reservoir 112 can have a tapered end 114 and tip 116. The reservoir 112 is pinned at 108 to first flange 104. Likewise a lever arm 124 is pinned at 110 to second flange 106. The plunger 120 is also pinned at 128 to a central portion of the lever arm 124. In use, the lever arm 124 is raised to draw the plunger 120 away for the tip 116, pulling fluid or air into the reservoir 112. To inject the fluid or air, the user applies pressure to the pad 126, forcing the plunger back into the reservoir. To compensate for the rotation of the reservoir 112, a cutout 102a can be placed on the front edge of the base 102.

Although preferred embodiments of the present invention have been described in the foregoing Detailed Description and illustrated in the accompanying drawings, it will be understood that the invention is not limited to the embodiments disclosed, but is capable of numerous rearrangements, modifications, and substitutions of parts and elements without departing from the spirit of the invention. Accordingly, the present invention is intended to encompass such rearrangements, modifications, and substitutions of parts and elements as fall within the scope of the appended claims.

We claim:

1. A power syringe comprising:
   (a) a reservoir having a plunger captured within;
   (b) a base having a flat surface and wherein a distal end of said reservoir is pivotally attached;
   (c) a first arm attached at one end to said plunger;
   (d) a second arm attached to said base, wherein said first arm is attached to a portion of said second arm such that movement of said second arm results in translation of the plunger into the reservoir.

2. The power syringe of claim 1 further comprises a threaded connector adjacent to a distal end of said reservoir.

3. The power syringe of claim 1 wherein said second arm further comprises:
   (e) a pad attached to said second arm.

4. The power syringe of claim 1 further comprises a plunger track to maintain a linear translation of said plunger.

5. The power syringe of claim 4 wherein said plunger track comprises a variable resistance path.

6. The power syringe of claim 1 wherein said reservoir is transparent.

7. The power syringe of claim 1 wherein said reservoir is marked with volume indicators.

8. The power syringe of claim 1 further comprises a travel limit which limits the downward travel of said second arm.

9. The power syringe of claim 1 further comprises a mechanical limit which limits the rearward travel of the plunger.

10. The power syringe of claim 1 further comprises a port in said reservoir to allow unwanted air to be removed.

* * * * *